United States Patent
Anelli et al.

(10) Patent No.: US 6,242,490 B1
(45) Date of Patent: Jun. 5, 2001

(54) USE OF CREATINE

(75) Inventors: Marco Anelli, Milan; Ettore Strumia, Turin, both of (IT)

(73) Assignee: Monsanto Italiano S.p.A., Milan (IT)

( * ) Notice: Subject to any disclaimer, the term of this patent is extended or adjusted under 35 U.S.C. 154(b) by 0 days.

(21) Appl. No.: 09/284,465

(22) PCT Filed: Nov. 10, 1997

(86) PCT No.: PCT/EP97/06225

§ 371 Date: Apr. 19, 1999

§ 102(e) Date: Apr. 19, 1999

(87) PCT Pub. No.: WO98/22099

PCT Pub. Date: May 28, 1998

(30) Foreign Application Priority Data

Nov. 19, 1996 (IT) ............................................. MI96A2408

(51) Int. Cl.⁷ ................................................. A61K 31/195

(52) U.S. Cl. ............................................................. 514/565
(58) Field of Search ............................................. 514/565

(56) References Cited

U.S. PATENT DOCUMENTS 4,371,521   2/1983   Izrael ..................................... 424/94

FOREIGN PATENT DOCUMENTS

9402127   *   2/1994   (WO) .
WO 98/00148   1/1998   (WO) .

OTHER PUBLICATIONS

Gordon, et al., "Creatine Supplementation in Chronic Heart Failure Increases Skeletal Muscle Creatine Phosphate and Muscle Performance" *Cardiovasc. Res.*, vol. 30, 1995, p. 413–418.

Volkov, et al., "Metabolic Correction of Psychic Disorders In Patients With Bronchial Asthma", *Allergy*, vol. 51, No. Suppl. 32, 1996, p. 98.

Scattolin et al., "Diastolic Function and Creatine Phosphate: An Echographic Study", *Current Therapeutic Research*, vol. 54, No. 5, 1993, p. 562–571.

Bichev, A.A., "The Effect of Exogenous Phosphocreatine on Function of Respiratory Muscles During Pulmonary Diseases", *Eur. Resp. J.*, vol. 7, No. S. 18, 1994, p. 343s.

Greenhaff et al. "Influence of Oral Creatine Supplementation of muscle torque during repeated Bouts Maximal Voluntary Exercise in Man", *Clinical Science*, vol. 84, 1993, p. 565–571.

Balsom et al., Creatine Supplementation per se Does Not Enhance Endurance Exercis Performance: *ACTA Physiol. Scand.*, vol. No. 149, 1993, p. 521–523.

Cafiero et al. "Efficacia della creatina fosfato nel trattamento dei pazienti con insufficienza cardiaca", *Clinical Therapeutical* vol., No. 4., 1994, p. 321–328.

Nagle, S., "Die Bedeutung von Kreatinphosphat und Adenosintripholt im Hinblick auf Energiebereitstellung, transport und–verwertung im normalen und insuffizienten Herzmusckel", *Klin. Wochenschrift*, vol. 48, No. 6, 1970, p. 332–341.

* cited by examiner

*Primary Examiner*—Theodore J. Criares
*Assistant Examiner*—Jennifer Kim
(74) *Attorney, Agent, or Firm*—Arent Fox Plotkin Kintner Kahn PLLC

(57) ABSTRACT

Description of a new use of creatine in the preparation of a drug for the treatment of cardiac and/or respiratory insufficiency.

2 Claims, 2 Drawing Sheets

USE OF CREATINE

Figure 1:
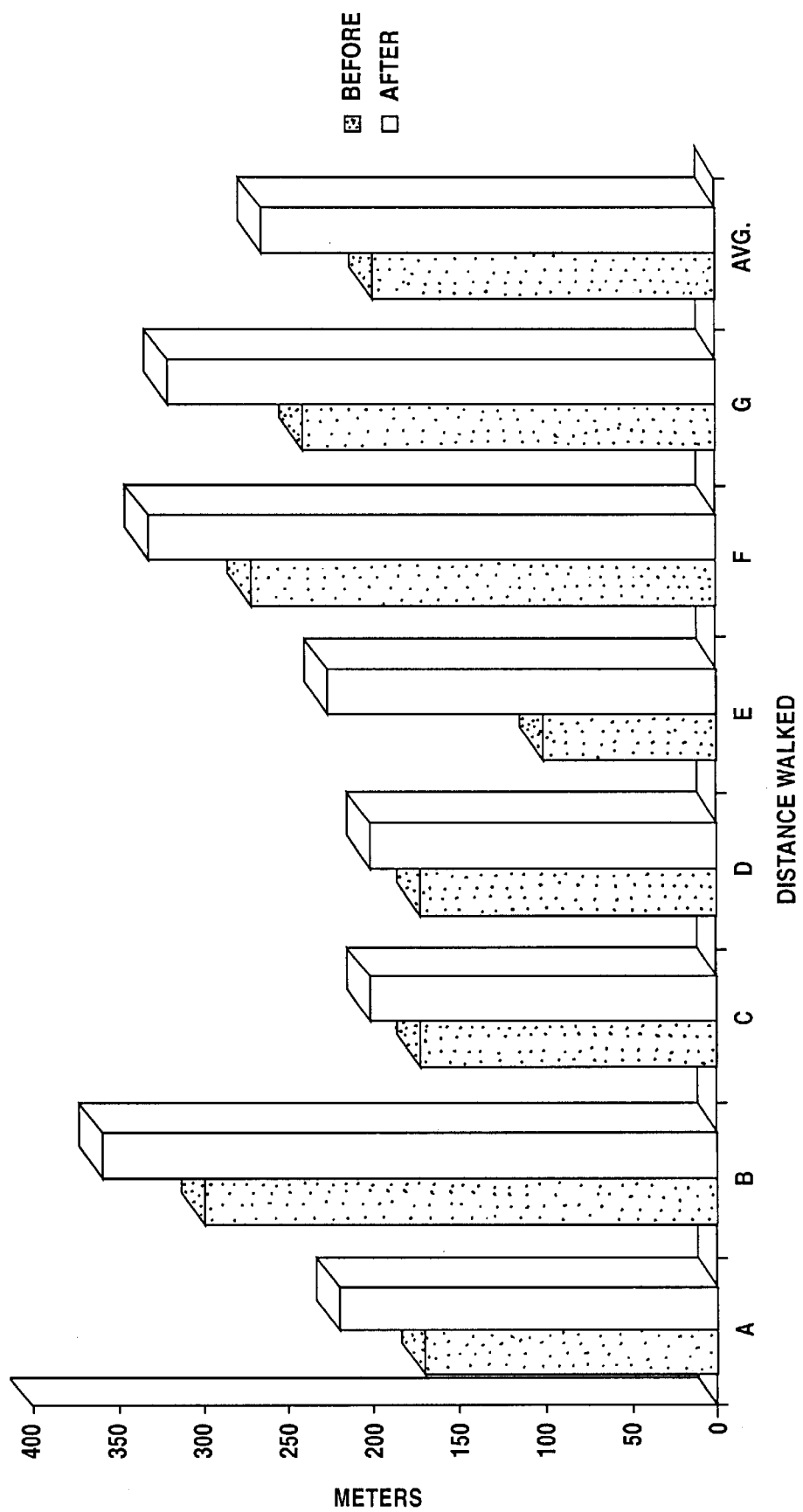

This invention refers to a new use of creatine, in particular in the preparation of a drug for the treatment of cardiac and/or respiratory insufficiency.

Creatine is a substance that plays an essential role in the metabolism of energy in humans and animals. A certain quantity of this vital compound is produced autonomously by our body, whereas a variable quantity is introduced through diet, basically through meat-based foods (J. B. Walker et al., in Adv. Enzymol. 1979, 50, 177–242).

It is well known that the assumption of exogenous creatine can improve the capacity to make brief and intense efforts (maximum exercise) both in normal subjects and in athletes (P. L. Greenhaff, in Clinical Science (1993), 84, 565–571; P. D. Balsom et al., in Scand. J. Med. Sci. Sports 1993, 3: 143–149).

Effects on the capacity to achieve maximum efforts have also been obtained using relatively high doses (15–20 g/die).

However, doses of this kind produce considerable collateral effects, such as gastrointestinal disorders, weight gain and water retention, representing a drawback to the prolonged use of creatine which is therefore not administered to improve the capacity of carrying out prolonged exercises (endurance) (P. D. Balsom et al., in Acta Physiol. Scand. 1993, 149, 521–523).

Moreover, the aforesaid doses, which are required to improve the capacity to perform maximum efforts, must be subdivided into several daily doses given that the administration of a single dose of more than 4–5 grams exceeds the so-called "renal threshold" and any excess substance is eliminated directly through urine without having performed any useful function at a systemic level.

The oral administration of creatine has been studied in patients suffering from cardiac insuffiency in whom it has shown a marked capacity to increase maximum effort.

Again in this case, however, the action of the substance was obtained at very high doses (15 g/die) (A. Gordon et al., in Cardiovascular Research 30 (1995) 413–418).

Owing to the aforesaid reasons, doses of this type cannot be used outside a closely contolled clinical trial performed for short periods.

It is clear that the collateral effects described earlier, which are evident in normal subjects, entail particularly high levels of risk for patients whose cardiovascular system is already damaged and/or fatigued by disease, thus representing a genuine obstacle to the administration of creatine.

Furthermore, compared to healthy subjects, the muscular energy metabolism of patients with heart and/or respiratory disorders is further damaged (B. M. Massie et al. in Circulation—vol.78, no. 2, 1988, 320–326; B. M. Massie et al., The American Journal of Cardiology, 1987, 60, 309–315) and treatment must not only take account of the general conditions, which are already critical owing to the underlying pathology, but also weigh up the negative effects of a reduced availability of energy.

Although the results of experiments in healthy subjects show that creatine doses of under 10–15 g/die are not efficacious, much lower doses (1–4 g/die) have been used as a food supplement in the diet of elderly, debilitated and/or vegetarian subjects with a marked antiasthenic effect.

Moreover, doses of this type have been much better tolerated for prolonged periods.

Surprisingly, it has now been found that creatine, administered at low doses (1–4 g/die), enables an improved efficiency of energy metabolism at a muscular level and also results in a general improvement in the exercise capacity of patients suffering from cardiac and/or respiratory insufficiency.

The subject of this invention is therefore the use of creatine in the preparation of a drug for the treatment of cardiac and/or respiratory insufficiency in which creatine is included at a dose ranging between 1 and 4 g/die.

In particular, it was surprisingly found that the use of creatine at the aforesaid doses was extremely beneficial for the preparation of a drug for the treatment of obstructive bronchopathies at an advanced stage.

The oral administration of the drug was found to be particularly well tolerated.

The drug prepared according to the method described by this invention can be realised using common pharmaceutical techniques and may include, in addition to a vehicle and/or pharmaceutically acceptable diluent, also one or more active ingredients, for example: amino acids, like arginine, valine, leucine and isoleucine, complex sugars and/or antioxidants.

The following example illustrates the invention but is in no way restrictive.

EXAMPLE

A trial was performed with seven patients suffering from advanced obstructive bronchopathy, 5 males and 2 females, mean age 67 years old; the patients were asked to perform the "walking test" in basal conditions. The test consisted in walking along a flat surface for 6 minutes.

For safety reasons, and also because of the need to collect data in real-time, heart rate and oxygen desaturation in venous blood were kept under constant control.

After 6 minutes, the distance walked, the final heart rate and oxygen desaturation were recorded for each patient.

At the end of each test, dyspnea, or in other words the breathing difficulties experienced by each patient, were evaluated using a special 12-point scale (known as "Borg's scale).

Patients were then administered a drug including 1 gram of creatine 3 times a day, at regular intervals, and the "walking test" was then repeated after 10 days' treatment.

After treatment all patients showed a marked increase in the distance covered.

This improvement, approximately 32% on average compared to basal levels, was highly significant (FIG. 1 shows, in histogram form, the distances walked by the seven patients and the relative mean: p=0.01) also following statistical analysis using Student's t-test for paired data.

The administration of low doses of creatine was therefore shown to be capable of improving these patients' resistance to prolonged effort.

Figure 2:
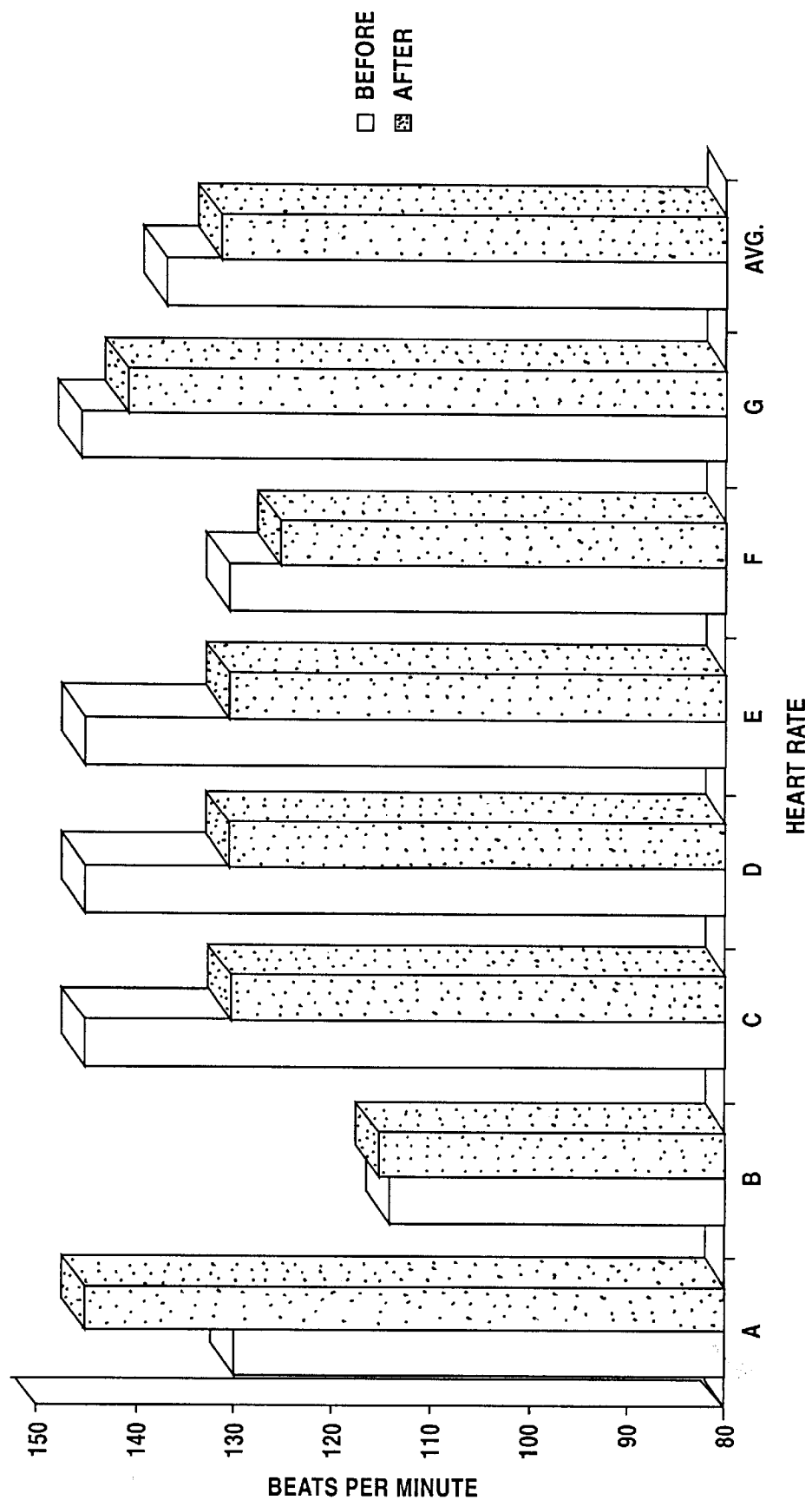

It was also unexpectedly found that all patients had completed the exercise protocol with a lower heart rate than that measured prior to creatine treatment with the sole exception of patient 1—excluded from the analysis of heart rate—who was only able to walk alone for 2 minutes in the preliminary test and 3 minutes in the final test. The mean reduction (which was also significant in the statistical tests performed using Student's t-test) was around 12 beats per minute (see FIG. 2 which shows, in histogram form, the heart rates of the seven patients and the relative mean).

The lesser involvement of the cardiovascular apparatus was also confirmed by the subjective reactions of patients.

Almost all of them showed a value on the Borg scale which was more than two points lower; no changes in hematic desaturation were reported.

The ascertainment of the lower involvement of the cardiovascular apparatus and the finding of a lower subjective perception of fatigue surprisingly showed that the administration of low doses of creatine substantially improves the efficiency of the energy metabolism at a muscular level.

This result is undoubtedly of considerable importance from a clinical point of view given that the administration of low doses of creatine to patients suffering from cardiac and/or respiratory insufficiency allows them to acquire greater autonomy of mobility, increased independence and a better quality of life.

What is claimed is:

1. A method for treating advanced obstructive bronchopathy in an adult patient comprising administering thereto creatine in effective amounts of between 1 and 4 g/day.

2. The method of claim 1 wherein the creatine is administered orally.

* * * * *

UNITED STATES PATENT AND TRADEMARK OFFICE
CERTIFICATE OF CORRECTION

PATENT NO. : 6,242,490 B1   Page 1 of 1
DATED : June 5, 2001
INVENTOR(S) : Marco Anelli et al.

It is certified that error appears in the above-identified patent and that said Letters Patent is hereby corrected as shown below:

Title page,
Please change the following: Item [73] "Monsanto Italiano S.p.A." to -- Monsanto Italiana S.p.A. --

Signed and Sealed this

First Day of January, 2002

Attest:

JAMES E. ROGAN
*Attesting Officer*   *Director of the United States Patent and Trademark Office*